(12) United States Patent
Chu et al.

(10) Patent No.: US 7,420,024 B2
(45) Date of Patent: Sep. 2, 2008

(54) PARTIALLY BIODEGRADABLE TEMPERATURE AND PH SENSITIVE HYDROGEL

(75) Inventors: Chih-Chang Chu, Ithaca, NY (US); Xian-Zheng Zhang, Wuhan (CN)

(73) Assignee: Cornell Research Foundation, Inc., Ithaca, NY (US)

( * ) Notice: Subject to any disclaimer, the term of this patent is extended or adjusted under 35 U.S.C. 154(b) by 340 days.

(21) Appl. No.: 10/537,354

(22) PCT Filed: Dec. 3, 2003

(86) PCT No.: PCT/US03/35985
§ 371 (c)(1),
(2), (4) Date: Jun. 6, 2005

(87) PCT Pub. No.: WO2004/064816
PCT Pub. Date: Aug. 5, 2004

(65) Prior Publication Data
US 2006/0128918 A1    Jun. 15, 2006

Related U.S. Application Data

(60) Provisional application No. 60/440,355, filed on Jan. 16, 2003.

(51) Int. Cl.
*C08F 251/00* (2006.01)

(52) U.S. Cl. .................................................. 527/300

(58) Field of Classification Search ................. 527/300
See application file for complete search history.

(56) References Cited

U.S. PATENT DOCUMENTS

| | | | | |
|---|---|---|---|---|
| 3,420,788 A * | 1/1969 | Solms | ........................ | 524/48 |
| 3,732,206 A * | 5/1973 | Kovats | ........................ | 536/108 |
| 3,870,664 A * | 3/1975 | Faulkner | ...................... | 527/300 |
| 3,884,909 A * | 5/1975 | Kightlinger et al. | ........... | 536/47 |
| 4,032,488 A * | 6/1977 | Hokkoku et al. | ......... | 526/238.2 |
| 4,777,232 A * | 10/1988 | Heidel | ........................ | 527/300 |
| 4,958,015 A * | 9/1990 | Zemel et al. | ................ | 536/103 |
| 4,963,629 A * | 10/1990 | Driemel et al. | ............. | 526/200 |
| 5,032,659 A * | 7/1991 | Heidel | ........................ | 527/300 |
| 5,055,501 A * | 10/1991 | Moriya et al. | ............... | 523/409 |
| 5,055,541 A * | 10/1991 | Floyd et al. | ................ | 527/300 |
| 5,128,461 A * | 7/1992 | Best et al. | ................... | 536/111 |
| 5,130,394 A * | 7/1992 | Nguyen et al. | .............. | 527/300 |
| 5,296,470 A * | 3/1994 | Vaslin et al. | .................. | 514/54 |
| 5,403,898 A * | 4/1995 | Bradshaw et al. | ........... | 525/474 |
| 5,603,955 A * | 2/1997 | Gehrke et al. | ............... | 424/484 |
| 5,616,671 A * | 4/1997 | Narayan et al. | ............. | 527/300 |
| 5,688,855 A * | 11/1997 | Stoy et al. | ................... | 524/505 |
| 5,714,540 A * | 2/1998 | Tanaka et al. | ............. | 525/54.24 |
| 5,780,568 A * | 7/1998 | Vuorenpaa et al. | .......... | 527/300 |
| 5,780,619 A * | 7/1998 | Lenz | ........................ | 536/123.1 |
| 6,211,315 B1 * | 4/2001 | Larock et al. | ............. | 526/238.3 |
| 6,339,116 B1 * | 1/2002 | Afzali-Ardakani et al. | .... | 524/72 |
| 6,388,047 B1 | 5/2002 | Won et al. | ................... | 528/354 |
| 6,458,889 B1 * | 10/2002 | Trollsas et al. | ............. | 525/54.1 |
| 6,476,204 B1 | 11/2002 | Kim et al. | ................... | 536/18.2 |
| 6,486,213 B1 * | 11/2002 | Chen et al. | ................ | 514/772.1 |
| 6,583,219 B2 | 6/2003 | Won et al. | ................... | 525/54.2 |
| 6,586,493 B1 * | 7/2003 | Massia et al. | ................ | 522/87 |
| 6,660,804 B1 * | 12/2003 | Weltrowski et al. | ....... | 525/54.23 |
| 6,841,644 B2 * | 1/2005 | Phillips et al. | .............. | 527/201 |
| 6,911,227 B2 * | 6/2005 | Hubbell et al. | ............. | 427/2.14 |
| 7,008,635 B1 * | 3/2006 | Coury et al. | ................. | 424/426 |
| 7,141,540 B2 * | 11/2006 | Wang et al. | ..................... | 514/1 |
| 2002/0015734 A1 * | 2/2002 | Uludag et al. | ................ | 424/486 |
| 2002/0068087 A1 * | 6/2002 | Marchant | .................... | 424/486 |
| 2002/0193516 A1 * | 12/2002 | Bucevschi et al. | .......... | 525/54.1 |
| 2003/0026841 A1 * | 2/2003 | Trubetskoy et al. | ......... | 424/486 |
| 2003/0094719 A1 * | 5/2003 | Yang et al. | ..................... | 264/41 |
| 2003/0152622 A1 * | 8/2003 | Louie-Helm et al. | ........ | 424/468 |
| 2004/0050513 A1 * | 3/2004 | Beckman et al. | ............ | 162/158 |
| 2004/0068073 A1 * | 4/2004 | Doane et al. | ................. | 527/300 |

OTHER PUBLICATIONS

Lewis, Richard J., Sr. (2002). Hawley's Condensed Chemical Dictionary (14th Edition). John Wiley & Sons.☐☐Online version available at: http://www.knovel.com/knovel2/Toc.jsp?BookID=704 &VerticalID=0.*

Zhang, Xianzheng, et al., "Synthesis and Characterization of Partially Biodegradable, Temperature and pH Sensitive Dex-MA/PNIPAAm Hydrogels", Biomaterials 25 (2004) 4719-4730.

Namkung, Sun, "Synthesis and Characterization of Partially Biodegradable Hydrogels as a Drug Delivery System", Thesis presented to the Graduate School of Cornell University, Jan. 2004.

* cited by examiner

*Primary Examiner*—Mark Eashoo
*Assistant Examiner*—Liam J Heincer
(74) *Attorney, Agent, or Firm*—Bacon & Thomas, PLLC

(57) ABSTRACT

Partially biodegradable hydrogel that changes its volume and shape in response to change in pH and/or temperature is prepared by UV irradiation of composition comprising dextran-maleic acid monoester and N-isopropylacrylamide.

6 Claims, 3 Drawing Sheets

PARTIALLY BIODEGRADABLE TEMPERATURE AND PH SENSITIVE HYDROGEL

CROSS-REFERENCE TO RELATED APPLICATIONS

This application claims the benefit of U.S. Provisional Patent Application No. 60/440,355, filed Jan. 16, 2003.

The invention was made at least in part with United States Government support under United States Department of Commerce Prime Grant Award No. 99-27-07400 pursuant to a subagreement with The National Textile Center. The United States Government has certain rights in the invention.

TECHNICAL FIELD

The invention relates to imparting temperature sensitive properties to polysaccharide-based, e.g., dextran-based, biomaterials.

BACKGROUND OF THE INVENTION

Biodegradable hydrogels formed by photocrosslinking dextran-maleic acid monoester hydrogel precursor are described in U.S. Pat. No. 6,476,204. These hydrogels are pH sensitive but are not temperature sensitive, i.e., their volume and structure are not affected by temperature change.

Temperature sensitive hydrogels are known. The most widely studied of these are poly(N-isopropylacrylamide) (PNIPAAm) hydrogels. These hydrogels have been indicated to exhibit a lower critical solution temperature (LCST) at about 33° C. PNIPAAm hydrogels are non-biodegradable.

SUMMARY OF THE INVENTION

It has been discovered herein that polysaccharide-maleic acid monoester precursors, e.g., dextran-maleic acid monoester precursors, can be used in conjunction with the temperature sensitive hydrogel precursor N-isopropylacrylamide (NIPAAm) as a co-precursor with the polysaccharide-maleic acid monoester not only functioning as the hydrogel precursor but also as the crosslinking agent, to form partially biodegradable smart hybrid hydrogels, i.e., partially biodegradable hydrogels that have decreased water retention with increased temperature and increased swelling ratio with increased pH. This allows release of an entrapped drug in the body (a) on increase to or near body temperature especially where the lower critical solution temperature (LCST) is exceeded by body temperature and (b) on an increase in pH in the hydrogel in the body. Thus the smart hybrid hydrogels herein are sensitive to external levels of increased temperature or to external levels of increased pH. The hydrogels are partially biodegradable because the polysaccharide-maleic acid monoester formed crosslinkages are biodegradable even though the poly(N-isopropylamide) chains are not so the hydrogels disassociate over time in vivo. It has also been discovered that by changing the feed composition ratios of the two types of precursors, the release properties of the hybrid hydrogels are controllable and the LCSTs can be adjusted to be at or near body temperature.

In one embodiment herein, the invention is directed to a hydrogel that is partially biodegradable and changes its shape and volume in response to change in pH and/or in response to change in temperature, formed by a method comprising photocrosslinking of dextran-maleic acid monoester and N-isopropylacrylamide in a composition comprising from 10 to 75% by weight dextran-maleic acid monoester and from 90% to 25% by weight N-isopropylacrylamide, with the total of the dextran-maleic acid monoester and N-isopropylacrylamide being 100%.

In another embodiment the invention is directed to a hydrogel forming system comprising a solution of from 10 to 75% by weight dextran-maleic acid monoester and from 90 to 25% by weight N-isopropylacrylamide based on the total of the dextran maleic acid monoester and the N-isopropylacrylamide being 100%.

The term "hydrogel" is used herein to mean a polymeric material which exhibits the ability to swell in water and to retain a significant portion of water within its structure without dissolution.

The term "biodegradable hydrogel" is used herein to mean hydrogel formed by cross-linking a polymer which is degraded by water and/or by enzymes found in nature. The term "partially biodegradable hydrogel" is used herein because while the dextran maleic acid monoester units biodegrade, the N-isopropylacrylamide units do not.

The term "hydrogel precursor" is used herein to mean polymer or other composition which in solution in a medium forms a hydrogel through photocrosslinking.

The term "photocrosslinking" is used herein to mean causing vinyl bonds to break and form cross-links by the application of radiant energy.

The lower critical solution temperature (LCST) of a hydrogel is the onset temperature of the endotherms and is the temperature above which the hydrogel collapses and the volume of the hydrogel shrinks dramatically.

DETAILED DESCRIPTION

Figure 1:
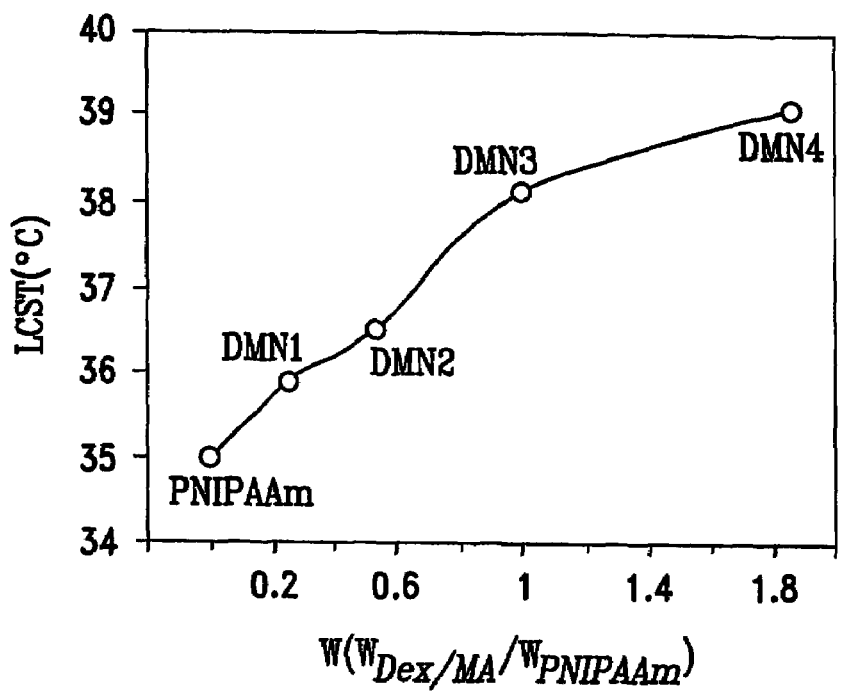
FIG. 1 is a graph of LSCT (° C.) versus weight ratio of Dex-MA to PNIPAAm and shows results of the working examples.

In one case, the hydrogel is formed by photocrosslinking dextran-maleic acid monoester (sometimes referred to as Dex-MA) and N-isopropylacrylamide in a composition comprising from 20 to 65% by weight dextran-maleic acid monoester and from 80% to 35% by weight, N-isopropylacrylamide, and in another case, a composition comprising 25 to 40% by weight dextran-maleic acid monoester and from 75% to 60% N-isopropylacrylamide.

The N-isopropylacrylamide is readily obtainable commercially.

The dextran-maleic acid monoester is that described in U.S. Pat. No. 6,476,204, the whole of which is incorporated herein by reference, and is a dextran-maleic acid monoester in which the average degree of substitution of each glucose unit of each α-D-glucopyranosyl of dextran by maleic acid ranges from 0.60 to 1.6 and which has a weight average molecular weight ranging from 40,000 to 80,000 on a dextran basis.

The term "degree of substitution" is used herein to mean the number of hydroxyl groups in a glucose unit of α-D-glucopyranosyl moiety of dextran that form ester group with maleic acid. Since each glucose unit contains three hydroxyl groups, the maximum degree of substitution is 3.0. The average degree of substitution connotes the average degree of substitution based on all the glucose units in the molecules of hydrogel precursor.

The term "on a dextran basis" is used herein to mean that the weight average molecular weight referred to is that of the dextran starting material for preparing the dextran-maleic acid monoester which provides the dextran moiety of the dextran-maleic acid monoester. The weight average molecule weights referred to herein are determined by gel permeation chromatography versus monodispersed polystyrene standards.

In one case the dextran-maleic monoester has an average degree of substitution ranging from 0.85 to 0.95 and a weight average molecular weight ranging from 65,000 to 75,000.

The dextran-maleic acid monoester precursors are readily prepared by reaction of dextran with maleic anhydride in the presence of a Lewis-base catalyst.

The reaction of dextran with maleic anhydride is preferably carried out in a dipolar aprotic solvent, e.g., N,N-dimethylformamide (DMF). LiCl is preferably included in the DMF reaction solvent to increase the solubility of dextran in DMF. The LiCl does this by forming a salt with DMF and thereby increases the polarity of the DMF.

The Lewis-base catalyst is preferably triethylamine (TEA).

The reaction can be carried out, for example, at a mole ratio of maleic anhydride to hydroxyl groups of dextran ranging from 0.3:1 to 3.0:1, a mole ratio of triethylamine (TEA) to maleic anhydride ranging from 0.001:1.0 to 0.10:1.0, reaction temperatures ranging from 20° C. to 80° C. and reaction times ranging from 1 hour to 20 hours or more.

Preparation of dextran-maleic acid monoester hydrogel precursor having an average degree of substitution ranging from 0.85 to 0.95 and a weight average molecular weight ranging from 65,000 to 75,000 is described in U.S. Pat. No. 6,476,204 at column 4, lines 13-29. Improvement of the method described in U.S. Pat. No. 6,476,204 has been found to be obtained by using a LiCl/dimethylformamide (50 wt %) solvent system, 0.06 moles of triethylamine to one mole of maleic anhydride instead of 0.10 moles of triethylamine to one mole of maleic anhydride and a reaction time of 16 hours instead of 8 hours.

We turn now to the preparation of the hydrogel from the dextran-maleic acid monoester and N-isopropylacrylamide hydrogel precursors. This preparation can be carried out as follows: The hydrogel precursors are dissolved in distilled water in appropriate weight ratios to give the concentrations denoted above, to make 10 to 30% (w/v) concentration solution, then photoinitiator, e.g., 2,2-dimethoxy 2-phenyl acetophenone, i.e., DMPAP, (e.g., in amount of 2-10% (w/w) of the hydrogel precursors), for example, in a solution in a protic solvent, e.g., N-methylpyrrolidone, tetrahydrofuran, dimethyl formamide or dimethyl sulfoxide, is added to the solution, and photocrosslinking is carried out by UV irradiation, e.g., at room temperature, for 5 to 30 hours. Unreacted chemicals are then preferably leached out of the resulting hydrogel. Drying of the hydrogel is preferably carried out by immersing in hot water (50° C.) for two hours to obtain shrinkage and drying the partially shrunk hydrogel in a vacuum oven at 60° C. for 5 to 15 hours, e.g. overnight.

The hydrogels of the invention are temperature sensitive, i.e., increase in temperature causes shrinking and water loss.

The hydrogels of the invention are pH sensitive, i.e., the swelling ratios of the hydrogels increase with increasing pH. The term "swelling ratio" is used with the definition set forth in U.S. Pat. No. 6,476,204.

The hydrogels herein are useful for the same purposes as are the hydrogels of U.S. Pat. No. 6,476,204. The temperature and pH sensitivity and the ability to change those by modifying feed composition allows for more control.

The lower critical solution temperature (LCST) of the hydrogels of the invention increase with increase in percentage of dextran-maleic acid monoester hydrogel precursor. When the hydrogels herein are used for biomedical applications in humans, it is preferred they have LCST less than or near (e.g., within 2 degrees C. of) body temperature.

The invention is supported by experiments and results and conclusions from those that are set forth in a manuscript titled "Design and Synthesis of Biodegradable and Intelligent Hydrogels" which is part of U.S. Provisional Patent Application No. 60/440,355, the whole of which is incorporated herein by reference The invention is illustrated by the following examples:

EXAMPLES I-V

For each example, the dextran maleic acid monoester was made up by dissolving dextran, 2.0 grams, weight average molecular weight of 69,800 (obtained fro Sigma Chemical Company) with 5% branching, in a LiCl/dimethylformamide (50 wt %) solvent system at 90° C. under nitrogen gas. After the dextran was clearly dissolved, the solution was cooled to 60° C. and then triethylamine was added in amount of 6 mol % to maleic anhydride to be added. The solution was stirred for 15 minutes. Then, maleic anhydride was added slowly to the solution in amount of 3.63 gm. The reaction was conducted at 60° C. for 16 hours under nitrogen. The reaction product was precipitated with cold isopropyl alcohol, filtered, washed several times with isopropyl alcohol, and then dried at room temperature in a vacuum oven. Dextran-maleic acid hydrogel precursor with a degree of substitution of 0.9 was obtained, i.e., 0.9 hydroxyl groups form ester groups with malic acid per dextran glucose ring.

Different weight ratios of dextran-maleic acid hydrogel precursor (Dex-MA) and N-isopropylacrylamide hydrogel precursor (NIPAAm) as set forth in Table 1 below were dissolved in distilled water to make 20% (w/v) concentration solutions. The photoinitiator, 2,2-dimethoxy 2-phenyl acetophenone (5% (w/w) of the hydrogel precursors) was first dissolved in N-methyl pyrrolidone (NMP), then mixed with the solution of the hydrogel precursors. The resulting homogeneous transparent mixture was irradiated using a portable long-wave UV lamp (365 nm, 8 W) at room temperature for 22 hours. The resultant hydrogels were first immersed in tetrahydrofuran (THF) at room temperature for 12 hours. During this period, the THF was replaced with fresh THF periodically in order to leach out unreacted chemicals. Then the hydrogels were further purified with distilled water for at least 48 hours and the distilled water was replaced every several hours to let the purified hydrogels reach equilibrium for characterization. The feed composition of precursors and other chemicals are listed in Table 1 below where the samples are all labeled DMN (D=dextran, M=maleic anhydride and N=NIPAAm) and samples DMN1, DMN2, DMN3, DMN4 and DMN5 respectively constitute Examples I, II, III, IV and V, NIPAAm is the N-isopropylacrylamide hydrogel precursor, Dextran-MA is dextran-maleic acid monoester hydrogel precursor and NMP is N-methylpyrrolidone and the percent conversion is the weight percentage of the synthesized gel from monomers.

TABLE 1

| | Sample Identification | | | | |
|---|---|---|---|---|---|
| | DMN1 | DMN2 | DMN3 | DMN4 | DMN5 |
| NIPAAm (mg) | 160 | 130 | 100 | 70 | 40 |
| Dextran-MA (mg) | 40 | 70 | 100 | 130 | 160 |
| H$_2$O (mL) | 1.0 | 1.0 | 1.0 | 1.0 | 1.0 |
| Photo-Initiator (mg) | 10.0 | 10.0 | 10.0 | 10.0 | 10.0 |
| NMP (ml) | 0.5 | 0.5 | 0.5 | 0.5 | 0.5 |
| Conversion (%) | 48.6 | 54.7 | 58.6 | 60.5 | 62.1 |

While DMN5 was obtained, its subsequent characterizations were not obtained because it disintegrated and/or dissocated in a water medium quickly, usually within 24 hours.

For comparison purposes, a 100% poly(N-isopropylacrylamide) hydrogel was synthesized and purified as described in Zhang, X. Z., et al., J. Colloid Interface Sci 246, 105-111 (2002). Briefly, 100 mg NIPAAm was dissolved in 1.2 ml water in the presence of 2.0 mg crosslinker, namely N,N'-methylbisacrylamide, using ammonium persulfate as the initiator and N,N,N',N'-tetramethylethylene diamine as the catalyst; polymerization was carried out at room temperature for 50 minutes.

The LCST property of the hydrogel samples was determined by using differential scanning calorimetry (TA2920 Modulated DSC, TA Instruments, USA). All samples were immersed in distilled water at room temperature for at least 2 days to reach a swollen state. About 10 mg swollen sample was placed inside a hermetic aluminum pan, and then sealed tightly by a hermetic aluminum lid. The thermal analyses were performed from 25 to 55° C. on the swollen hydrogel samples under a dry nitrogen atmosphere with a flow rate of 25 ml/min and a heating rate of 3° C./min. The LCSTs of the hydrogel samples determined as described above are shown in FIG. 1 which depicts the LCST as a function at the weight ratio of Dex-MA to PNIPAAm. The data indicate that all the samples had a higher LCST than pure PNIPAAm (about 35° C.) and that increase of Dex-MA percentage resulted in increased LCST (LCST of PNIPAAm=about 35° C., LCST of DMN1=35.9°; LCST of DMN2=36.5°; LCST of DMN3=38.1° C.; and LCST of DMN4=39.1° C.). This observed increasing LCST with increasing Dex-MA percentage was also associated with a reduction in enthalpy values (ΔH for DMN1=0.61 mJ/mg to ΔH for DMN4=0.14 mJ/mg).

The interior morphology of the hydrogel samples was determined as follows: The samples after reaching their maximum swelling ratio in distilled water at room temperature were quickly frozen in liquid nitrogen and then freeze dried in a Vertis Freeze Drier (Gardiner, N.Y.) under vacuum at −42° C. for three days until all water was sublimed. The freeze-dried samples were each fractured carefully under liquid N$_2$ temperature and the interior morphology of resulting pieces was studied with a scanning electron microscope (Hitachi S4500SEM, Mountain View, Calif.). Before SEM observation, the specimens were fixed on aluminum stubs and coated with gold. In each case a honeycomb structure was observed but the pore structure changed from an irregular round and loose shallow pores having wavy thin walls in PNIPAAm to a very well defined honeycomb structure with sharp distinctive angles and 4 to 7 member ring rigid wall pores in the hybrid hydrogels. The average pore size and pore number per unit area are given in Table 2 below:

TABLE 2

| | PNIPAAm | DMN1 | DMN2 | DMN3 | DMN4 |
|---|---|---|---|---|---|
| Pore diameter (μm) | 15 ± 5 | 13 ± 5 | 10 ± 4 | 6 ± 2 | 3 ± 1 |
| Pore number per 400 μm$^2$ | 1.8 | 2.4 | 4.0 | 11.1 | 44.4 |

As indicated in Table 2, the pore size decreased with increase in Dex-MA content.

Figure 2:
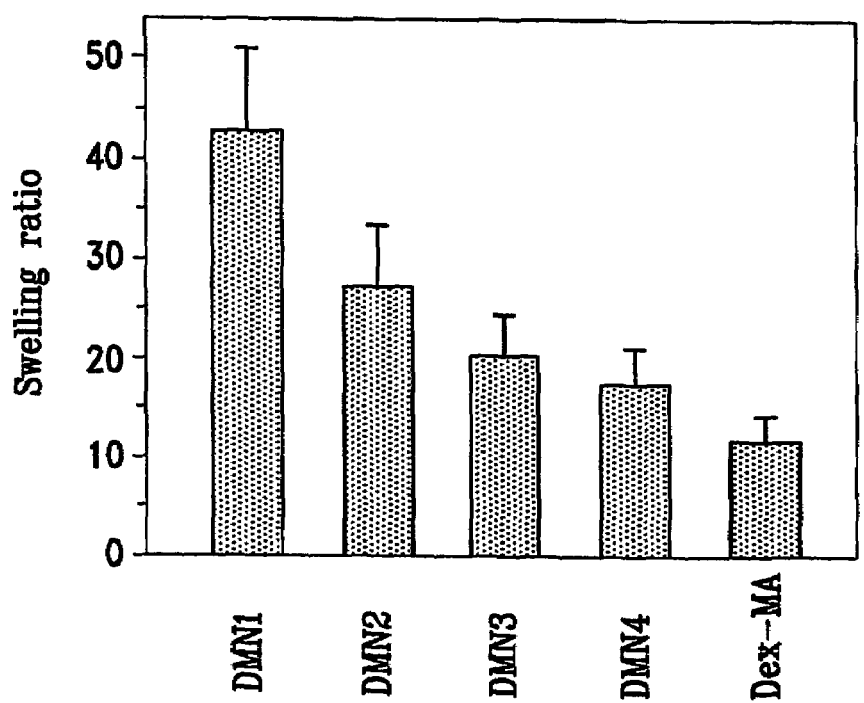
FIG. 2 is a graph of swelling ratio versus sample designation and shows results of the working examples.

Maximum swelling ratios at room temperature were determined by immersing samples in distilled water for 48 hours and measuring gravimetrically. Three measurements were taken for each sample. The term "swelling ratio" is used herein to mean weight of water in swollen gel per the dried weight of the gel before swelling. The maximum swelling ratios obtained at room temperature, are set forth in FIG. 2. As indicated in FIG. 2, maximum swelling ratio of the hydrogels decreased with increasing Dex-MA content.

Figure 3:
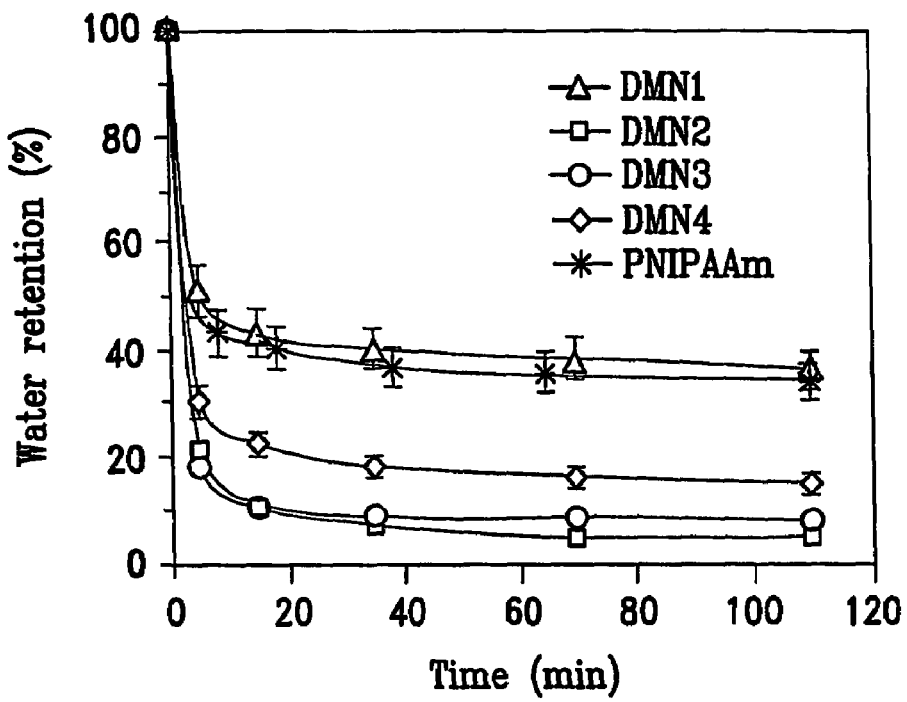
FIG. 3 depicts water retention values versus time for the various samples and shows results of the working examples.

Temperature response kinetics were determined by measuring at 50° C. gravimetrically. The temperatures were selected to be well above the LCST of the hydrogel so dramatic changes in volume and water content could be obtained in a short time frame. Before the measurements, the hydrogel samples were immersed in distilled water at room temperature for 24 h. The samples were then transferred to 50° C. distilled water bath. The weight changes of gels were recorded at regular time intervals. Water retention values were determined to show the temperature sensitivity of the hydrogels. Water retention values determined are set forth in FIG. 3. The water retention (WR) is defined as $100 \times [(W_t - W_d)/W_s]$ where $W_t$ is the weight of hydrogel at a given time interval and the other symbols are the same as defined for swelling ratio at room temperature. The data indicate that incorporation of PNIPAAm into dextran-based hydrogels provides thermo-responsive capability not present before. The rate of thermo-responsive capability varied with the composition ratio of Dex-MA to PIPAAm precursors. Whereas a reduction in thermo-response extent was expected with incorporation of Dex-MA, the opposite was determined to be the case for DMN2, DMN3 and DMN4. Sample DMN1 was considered to be an exception because of bubbles supporting a dense skin layer on the surface which prevented water loss, perhaps because of insufficient Dex-MA content.

Figure 4:
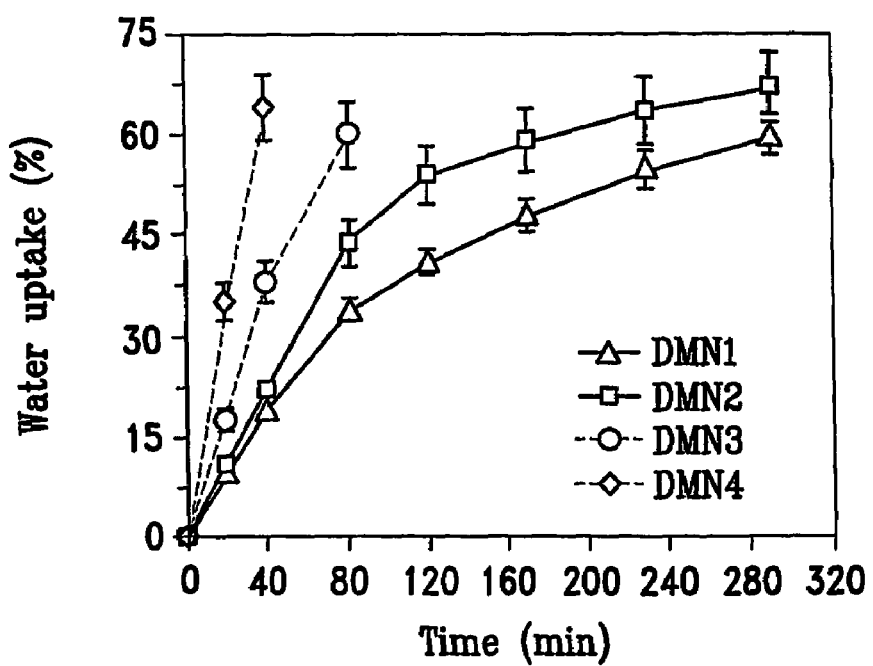
FIG. 4 depicts water uptake values versus time for samples and shows results of working examples.

Swelling kinetics of the hydrogels were defined in terms of water uptake (WU) which was defined as $100 \times [(W_t - W_d)/W_s]$ where the symbols are the same as above. Testing was carried out as follows: Swollen gel samples were first immersed in hot water (50° C.) for 2 h, then the shrunk hydrogel was further dried in a vacuum oven at 60° C. overnight until the gel weight was constant. Then, the swelling kinetics of the dried gel was measured gravimetrically at 22° C. Samples were taken from the hot water at regular time intervals. After wiping off the water on the surfaces with moistened filter paper, the weight of gels was recorded. Water uptakes were then determined. The results are shown in FIG. 4. As shown in said FIG. 4, if the Dex-MA content is high (DMN3 and DMN4), the hydrogels disintegrate in water quickly without reaching maximum water uptake. For the other samples, as the percentage of the Dex-MA increased, rate of water uptake increased.

Figure 5:
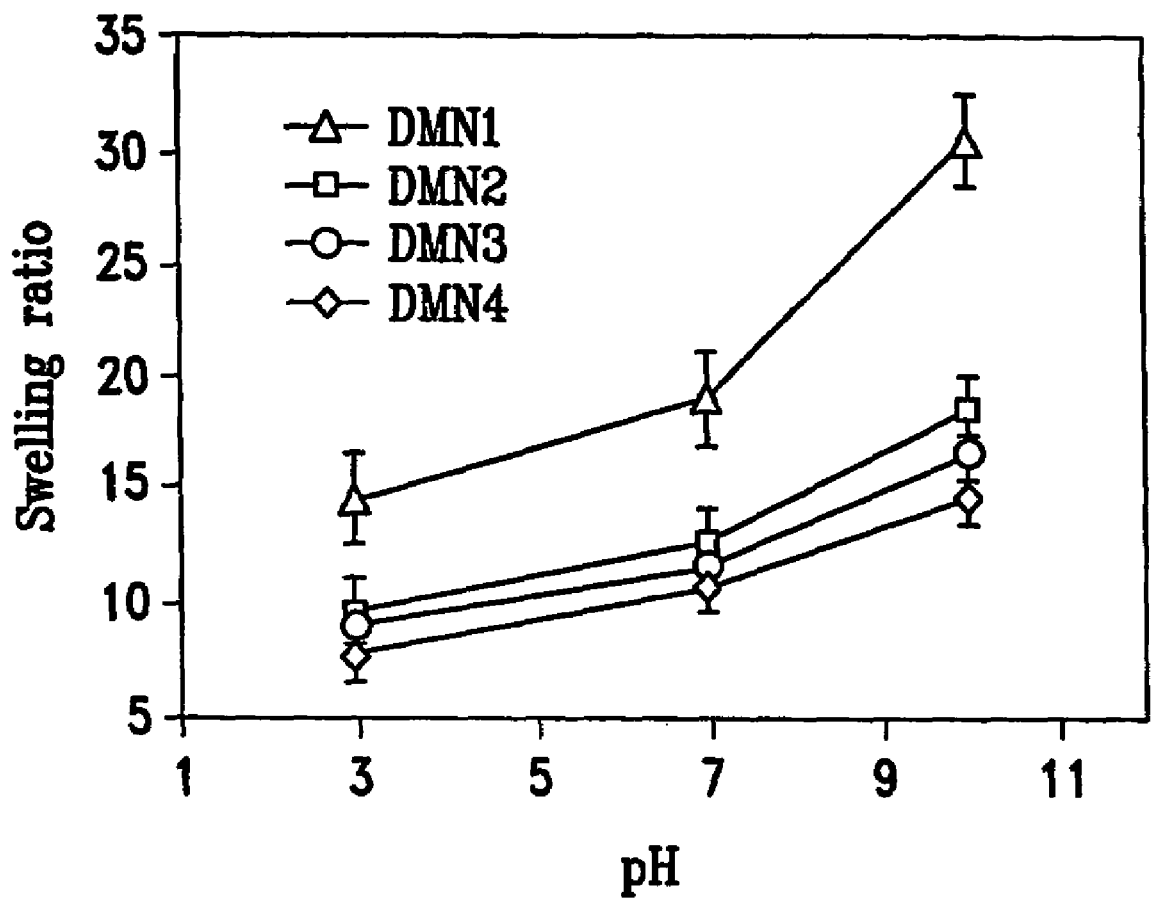
FIG. 5 depicts swelling versus pH for samples and shows results of working examples.

The pH sensitivity of the hydrogels was determined by immersing hydrogels in buffer solutions with pH values of 3, 7 and 10. Soaked hydrogel was removed at a predetermined interval, washed, surface water was wiped with wet filter paper and weighing was carried out until stable weight was detected. Swelling ratio (as defined above and measured as described above) results are set forth in FIG. 5. The data shows increasing swelling ratio with increasing of pH.

The data demonstrates temperature sensitivity as well as pH sensitivity and that the phase transition temperature (LCST) can be modulated to be near body temperature.

Variations

Variations of the above will be evident to those skilled in the art. Therefore, the scope of the invention is defined by the claims.

What is claimed is:

1. Hydrogel that changes its shape and volume in response to change in pH and in response to change in temperature, formed by photocrosslinking of dextran-maleic acid monoester and N-isopropylacrylamide in a composition comprising from 10 to 75% by weight dextran-maleic monoester and from 90 to 25% by weight N-isopropylacrylamide, with the total of the dextran-maleic acid monoester and N-isopropylacrylamide being 100%.

2. The hydrogel of claim 1 which is formed by photocrosslinking dextran-maleic acid monoester and N-isopropylacrylamide in a composition comprising from 20 to 65% by weight dextran-maleic acid monoester and from 80 to 35% by weight N-isopropylacrylamide.

3. The hydrogel of claim 2 where the dextran-maleic acid monoester has an average degree of substitution ranging from 0.85 to 0.95 and a weight average molecular weight ranging from 65,000 to 75,000 on a dextran basis.

4. The hydrogel of claim 3 which has a lower critical solution temperature which is less than or near body temperature.

5. A hydrogel forming system comprising a solution of from 10 to 75% by weight dextran-maleic acid monoester and from 90 to 25% by weight N-isopropylacrylamide based on the total of the dextran-maleic acid monoester and the N-isopropylacrylamide being 100%.

6. Hydrogel formed by photocrosslinking of dextran-maleic acid monoester and N-isopropylacrylamide in a composition comprising from 10 to 75% by weight dextran-maleic acid monoester to provide functionality for the hydrogel to change shape and volume in response to pH change and from 90 to 25% by weight N-isopropylacrylamide to provide functionality for the hydrogel to change shape and volume in response to temperature change, the total of the dextran-maleic acid monoester and N-isopropylacrylamide being 100%.

* * * * *